(12) United States Patent
Kagawa et al.

(10) Patent No.: US 8,568,673 B2
(45) Date of Patent: Oct. 29, 2013

(54) GAS ANALYSIS DEVICE, MERCURY REMOVAL SYSTEM, GAS ANALYSIS METHOD, AND REMOVAL METHOD FOR MERCURY IN FLUE GAS

(75) Inventors: Seiji Kagawa, Tokyo (JP); Masaru Chiyomaru, Tokyo (JP); Nobuyuki Ukai, Tokyo (JP); Takuya Okamoto, Tokyo (JP); Moritoshi Murakami, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 13/807,196

(22) PCT Filed: Sep. 22, 2011

(86) PCT No.: PCT/JP2011/071710
§ 371 (c)(1),
(2), (4) Date: Dec. 27, 2012

(87) PCT Pub. No.: WO2012/043411
PCT Pub. Date: Apr. 5, 2012

(65) Prior Publication Data
US 2013/0101487 A1 Apr. 25, 2013

(30) Foreign Application Priority Data
Sep. 28, 2010 (JP) .................. 2010-217909

(51) Int. Cl.
*B01D 53/46* (2006.01)
*B01D 53/50* (2006.01)
*B01D 53/56* (2006.01)
*B01D 53/64* (2006.01)
*B01D 53/74* (2006.01)
*B01D 53/75* (2006.01)
*B01D 53/78* (2006.01)
*B01D 53/79* (2006.01)
*B01D 53/86* (2006.01)
*B01D 53/90* (2006.01)
*G01N 23/00* (2006.01)
*G01T 1/00* (2006.01)

(52) U.S. Cl.
USPC ............... 423/210; 423/215.5; 423/239.1; 423/243.08; 422/62; 422/68.1; 422/105; 422/108; 422/111; 422/168; 422/169; 422/170; 422/171; 422/172; 422/177; 700/266; 700/271; 250/458.1; 378/45

(58) Field of Classification Search
USPC ............ 423/210, 215.5, 239.1, 243.08; 422/105, 108, 111, 168–172, 177, 62, 422/68.1; 700/266, 271; 250/458.1; 378/45
See application file for complete search history.

(56) References Cited

U.S. PATENT DOCUMENTS

| | | | |
|---|---|---|---|
| 3,578,410 A * | 5/1971 | Van Luik, Jr. .................. 436/36 |
| 7,622,092 B2 * | 11/2009 | Honjo et al. ................... 423/210 |
| 2003/0235525 A1 * | 12/2003 | Honjo et al. ................... 423/210 |
| 2007/0202020 A1 * | 8/2007 | Honjo et al. ................... 422/177 |
| 2008/0138264 A1 | 6/2008 | Honjo et al. |
| 2010/0074817 A1 | 3/2010 | Kobayashi et al. |
| 2011/0002829 A1 * | 1/2011 | Ukai et al. .................. 423/239.1 |
| 2011/0162345 A1 | 7/2011 | Nochi et al. |
| 2012/0189521 A1 * | 7/2012 | Shijo et al. ................. 423/239.1 |

FOREIGN PATENT DOCUMENTS

| | | |
|---|---|---|
| JP | 63-18251 A | 1/1988 |
| JP | 7-270284 A | 10/1995 |
| JP | 9-280540 A | 10/1997 |
| JP | 2003-14625 A | 1/2003 |
| JP | 2007-167743 A | 7/2007 |
| JP | 2008-142602 A | 6/2008 |
| JP | 2009-202107 A | 9/2009 |
| JP | 2010-36157 A | 2/2010 |
| JP | 2010-221150 A | 10/2010 |
| WO | 2008/078722 A1 | 7/2008 |

OTHER PUBLICATIONS

International Search Report for PCT/JP2011/071710, mailing date of Dec. 13, 2011.

* cited by examiner

*Primary Examiner* — Timothy Vanoy

(74) *Attorney, Agent, or Firm* — Westerman, Hattori, Daniels & Adrian, LLP

(57) ABSTRACT

A gas analysis device according to the present invention includes a flue-gas extraction pipe for extracting flue gas from a flue gas duct to which flue gas including both of $NH_4Cl$ and $SO_3$ is fed, a collector that is provided in the flue-gas extraction pipe, for removing soot dust contained in the extracted flue gas, a roll filter that is provided in the flue-gas extraction pipe, for depositing both of $NH_4Cl$ and $SO_3$ contained in the flue gas, and a measurement device for measuring both of $NH_4Cl$ and $SO_3$ contained in the flue gas by irradiating a sample including both of $NH_4Cl$ and $SO_3$ deposited by the roll filter with X-rays and detecting fluorescent X-rays generated from the sample.

7 Claims, 6 Drawing Sheets

GAS ANALYSIS DEVICE, MERCURY REMOVAL SYSTEM, GAS ANALYSIS METHOD, AND REMOVAL METHOD FOR MERCURY IN FLUE GAS

FIELD

The present invention relates to a gas analysis device, a mercury removal system, a gas analysis method, and a removal method for mercury in flue gas that enable to measure a concentration of ammonium chloride supplied into flue gas of a boiler.

BACKGROUND

Harmful substances such as soot dust, sulfur oxides (SOx), and nitrogen oxides (NOx) are contained in flue gas emitted from combustion facilities such as a boiler and a waste combustor and need to be removed by using a flue-gas treatment device. A typical flue-gas treatment device includes a denitrator that reduces NOx and a wet desulfurizer that uses an alkali absorbent as a SOx absorbing agent. The flue-gas treatment device treats harmful substances contained in flue gas by supplying ammonia ($NH_3$) on an upstream side of the denitrator in a flue gas duct to reduce nitric oxide (NO) with a denitration catalyst of the denitrator to remove NOx as shown in the following formula (1) and absorbing SOx in the alkali absorbent by using the wet desulfurizer (see, for example, Patent Literature 1).

$$4NO+4NH_3+O_2+4N_2+6H_2O \quad (1)$$

SOx includes $SO_2$ and $SO_3$. When a gas temperature of the flue gas reduces, $SO_2$ and $SO_3$ may change into ammonium hydrogen sulfate or ammonium sulfate as shown in the following formulas (2) and (3), and attach to the wall surface of the flue gas duct or devices that are installed in the flue gas duct. The ammonium hydrogen sulfate, the ammonium sulfate, and the like may cause clogging of an element of an air heater due to attachment thereto. Furthermore, the ammonium hydrogen sulfate and the ammonium sulfate are corrosive substances and thus the wall surface or the devices may corrode when these substances are attached thereto.

$$NH_3+SO_3+H_2O=NH_4HSO_4 \quad (2)$$

$$2NH_3+SO_3+H_2O=(NH_4)_2SO_4 \quad (3)$$

To reduce NOx, $NH_3$ is supplied in the upstream step of the denitrator. However, $NH_3$ is used for neutralization of $SO_3$ and thus the supply amount of $NH_3$ also needs to be adjusted.

Accordingly, gas analysis methods that enable to extract a part of flue gas, and perform a ultraviolet absorption analysis to analyze $SO_3$ and $NH_3$ in the flue gas and to measure concentrations of $SO_3$ and $NH_3$ in the flue gas have been conventionally proposed (see, for example, Patent Literature 2).

Coal-combustion flue gas or flue gas produced when heavy oil is combusted may contain metallic mercury ($Hg^0$) in addition to soot dust, SOx, and NOx. Recently, methods or devices that enable to treat the metallic mercury ($Hg^0$) by using a combination of the denitrator that reduces NOx and the wet desulfurizer that absorbs SOx have been variously developed.

As examples of the method that enables to treat the metallic mercury ($Hg^0$) in flue gas, methods of spraying an $NH_4Cl$ solution in a liquid form on the upstream side of a reduction denitrator in a flue gas duct to supply the solution into the flue gas duct are proposed (see, for example, Patent Literatures 3 and 4). When the $NH_4Cl$ solution is sprayed in a liquid form into the flue gas duct, $NH_4Cl$ dissociates into ammonia ($NH_3$) gas and hydrochloric acid (HCl) gas. The $NH_3$ gas acts as a reductant and the HCl gas acts as a mercury chlorinating agent. That is, on a denitration catalyst filled in the reduction denitrator, $NH_3$ has a reduction reaction proceeding with NOx in the flue gas as shown in the formula (1) and HCl has a reduction reaction proceeding with $Hg^0$ in the flue gas as shown in the following formula (4). After $NH_3$ is reductively denitrated on the denitration catalyst and the metallic mercury ($Hg^0$) is oxidized to an aqueous mercury chloride ($HgCl_2$), $HgCl_2$ is dissolved with water by a wet desulfurizer installed on the downstream side to remove mercury contained in the flue gas, and SOx contained in the flue gas is absorbed and removed.

$$Hg^0+\tfrac{1}{2}O_2+2HCl \rightarrow HgCl_2+H_2O \quad (4)$$

CITATION LIST

Patent Literatures

Patent Literature 1: Japanese Patent Application Laid-open No. 9-028054
Patent Literature 2: Japanese Patent Application Laid-open No. 2003-014625
Patent Literature 3: Japanese Patent Application Laid-open No. 2008-142602
Patent Literature 4: Japanese Patent Application Laid-open No. 2009-202107

SUMMARY

Technical Problem

However, when the $NH_4Cl$ solution is sprayed in a liquid form into the flue gas duct to oxidize $Hg^0$ contained in the flue gas to be treated in the desulfurizer, the conventional gas analysis method that enables to measure the concentrations of $SO_3$ and $NH_3$ in the flue gas as described in Patent Literature 2 cannot analyze chlorine ions ($Cl^-$) resulting from HCl generated by dissociation of $NH_4Cl$. That is, when a device that supplies the $NH_4Cl$ solution to oxidize $Hg^0$ contained in the flue gas is added to a conventional flue-gas treatment device having a device that supplies $NH_3$ into the flue gas duct and when the concentration of $NH_3$ in the flue gas is measured as in the conventional technique as described in Patent Literature 2, whether a value of the $NH_3$ concentration obtained from analysis depends on the concentration of $NH_3$ supplied by the device that supplies $NH_3$ or on the concentration of $NH_3$ supplied by the device that supplies the $NH_4Cl$ solution cannot be determined.

Accordingly, a gas analysis device that enables to measure also a concentration of $Cl^-$ contained in the flue gas to determine a supply amount of the $NH_4Cl$ solution has been demanded.

The present invention has been achieved in view of the above problems and an object of the present invention is to provide a gas analysis device, a mercury removal system, a gas analysis method, and a removal method for mercury contained in flue gas that enable to measure a concentration of $Cl^-$ contained in the flue gas.

Solution to Problem

According to a first aspect of the present invention in order to solve the above problems, there is provided a gas analysis device including: a flue-gas extraction pipe that extracts, from a flue gas duct, flue gas that is emitted from a boiler and to which ammonium chloride is supplied; soot-dust removal unit that is provided in the flue-gas extraction pipe and removes soot dust contained in the extracted flue gas; a deposition unit that is provided in the flue-gas extraction pipe and deposits the ammonium chloride contained in the flue gas; and a measurement unit that measures the ammonium chloride contained the flue gas by detecting fluorescent X-rays generated by irradiation of the ammonium chloride deposited by the deposition unit with X-rays or laser beams.

According to a second aspect of the present invention, there is provided the gas analysis device according to the first aspect, wherein the flue gas further contains sulfurous acid, the deposition unit deposits sulfurous acid, and the measurement unit measures sulfurous acid.

According to a third aspect of the present invention, there is provided the mercury removal system that removes mercury contained in flue gas that is emitted from a boiler, the mercury removal system including: an ammonium-chloride supply unit that sprays a solution containing ammonium chloride into a flue gas duct of the boiler; a reduction denitrator that has a denitration catalyst reducing nitrogen oxides in the flue gas with ammonia and oxidizing mercury in coexistence of hydrogen chloride; a wet desulfurizer that removes the mercury oxidized in the reduction denitrator using an alkali absorbent; and an ammonium-chloride-concentration measurement unit that is provided on either one or both of upstream and downstream sides of the reduction denitrator and analyzes a concentration of the ammonium chloride contained in the flue gas, wherein the gas analysis device according to claim 1 is used as the ammonium-chloride-concentration measurement unit, and a spray amount of the solution containing the ammonium chloride is controlled according to the concentration of the ammonium chloride obtained by the ammonium-chloride-concentration measurement unit.

According to a fourth aspect of the present invention, there is provided the mercury removal system according to the third aspect, having a heat exchanger that is provided between the reduction denitrator and the wet desulfurizer and performs heat exchange with the flue gas having passed through the reduction denitrator for heat recovery, wherein a gas temperature of the flue gas that passes through the heat exchanger is controlled based on a relation between ammonium chloride concentrations and gas temperatures, which are obtained in advance.

According to a fifth aspect of the present invention, there is provided the mercury removal system according to the third aspect, having a heat exchanger that is provided between the reduction denitrator and the wet desulfurizer and performs heat exchange with the flue gas having passed through the reduction denitrator for heat recovery, wherein the gas analysis device according to claim 2 is used as the ammonium-chloride-concentration measurement unit, and a gas temperature of the flue gas passing through the heat exchanger is controlled based on either one or both of a relation between ammonium chloride concentrations and gas temperatures and a relation between sulfurous acid concentrations and gas temperatures, which are obtained in advance.

According to a sixth aspect of the present invention, there is provided a gas analysis method that enables to extract, from a flue gas duct, flue gas that is emitted from a boiler and to which ammonium chloride is supplied, remove soot dust contained in the flue gas, deposit the ammonium chloride contained in the flue gas, then cause the deposited ammonium chloride to be contained in analysis gas, extract the analysis gas, and measure the ammonium chloride contained in the analysis gas.

According to a seventh aspect of the present invention, there is provided the gas analysis method according to the sixth aspect, wherein the flue gas further contains sulfurous acid, the sulfurous acid is deposited in addition to the ammonium chloride, and the deposited sulfurous acid is measured.

According to an eighth aspect of the present invention, there is provided the mercury removal method that enables to remove mercury contained in flue gas emitted from a boiler, the removal method for mercury contained in flue gas including: an ammonium-chloride supply step of spraying a solution containing ammonium chloride into a flue gas duct of the boiler; a reduction denitration step of including a denitration catalyst that reduces nitrogen oxides in the flue gas with ammonia and oxidizes mercury in coexistence of hydrogen chloride; a wet desulfurization step of removing the mercury oxidized at the reduction denitration step using an alkali absorbent; and an ammonium-chloride-concentration measurement step of analyzing a concentration of the ammonium chloride contained in the flue gas on either one or both of upstream and downstream sides of the reduction denitrator, wherein the gas analysis method according to claim 6 is used at the ammonium-chloride-concentration measurement step, and a concentration of the ammonium chloride contained in the flue gas is obtained at the ammonium-chloride-concentration measurement step, and a spray amount of the solution containing the ammonium chloride is controlled according to the obtained concentration of the ammonium chloride.

According to a sixth aspect of the present invention, there is provided the removal method for mercury in flue gas according to the eighth aspect, including: a heat recovery step of performing heat exchange between the flue gas and a heating medium circulating in a heat exchanger between the reduction denitration step and the wet desulfurization step; and a reheat step of reheating cleaned gas emitted from the wet desulfurizer by performing heat exchange between the cleaned gas and the heating medium, wherein the gas analysis method according to claim 6 is used at the ammonium-chloride-concentration measurement step, and a gas temperature of the flue gas to be subjected to heat exchange with the heating medium at the heat recovery step is controlled based on a relation between ammonium chloride concentrations and gas temperatures, which are obtained in advance.

According to a tenth aspect of the present invention, there is provided the removal method for mercury in flue gas according to the eight aspect, including: a heat recovery step of performing heat exchange between the flue gas and a heating medium circulating in a heat exchanger between the reduction denitration step and the wet desulfurization step; and a reheat step of reheating cleaned gas emitted from the wet desulfurizer by performing heat exchange between the cleaned gas and the heating medium, wherein the gas analysis method according to the seventh aspect is used at the ammonium-chloride-concentration measurement step, and a gas temperature of the flue gas subjected to heat exchange with the heating medium at the heat recovery step is controlled based on either one or both of a relation between ammonium chloride concentrations and gas temperatures and a relation between sulfurous acid concentrations and gas temperatures, which are obtained in advance.

Advantageous Effects of Invention

According to the present invention, ammonium chloride contained in flue gas is deposited and then the deposited ammonium chloride is analyzed to measure a concentration of Cl⁻ contained in the flue gas, thereby enabling to obtain a concentration of the ammonium chloride contained in the flue gas.

DESCRIPTION OF EMBODIMENTS

Modes for preferably carrying out the present invention (hereinafter, "embodiment") will be explained below in detail with reference to the accompanying drawings. The present invention is not limited to the contents of the following embodiments. Constituent elements in the following embodiments include those that can be easily anticipated by persons skilled in the art, that are substantially identical, or that are in a so-called range of equivalents. Furthermore, constituent elements disclosed in the following embodiments can be combined as appropriate.

First Embodiment

Figure 1:
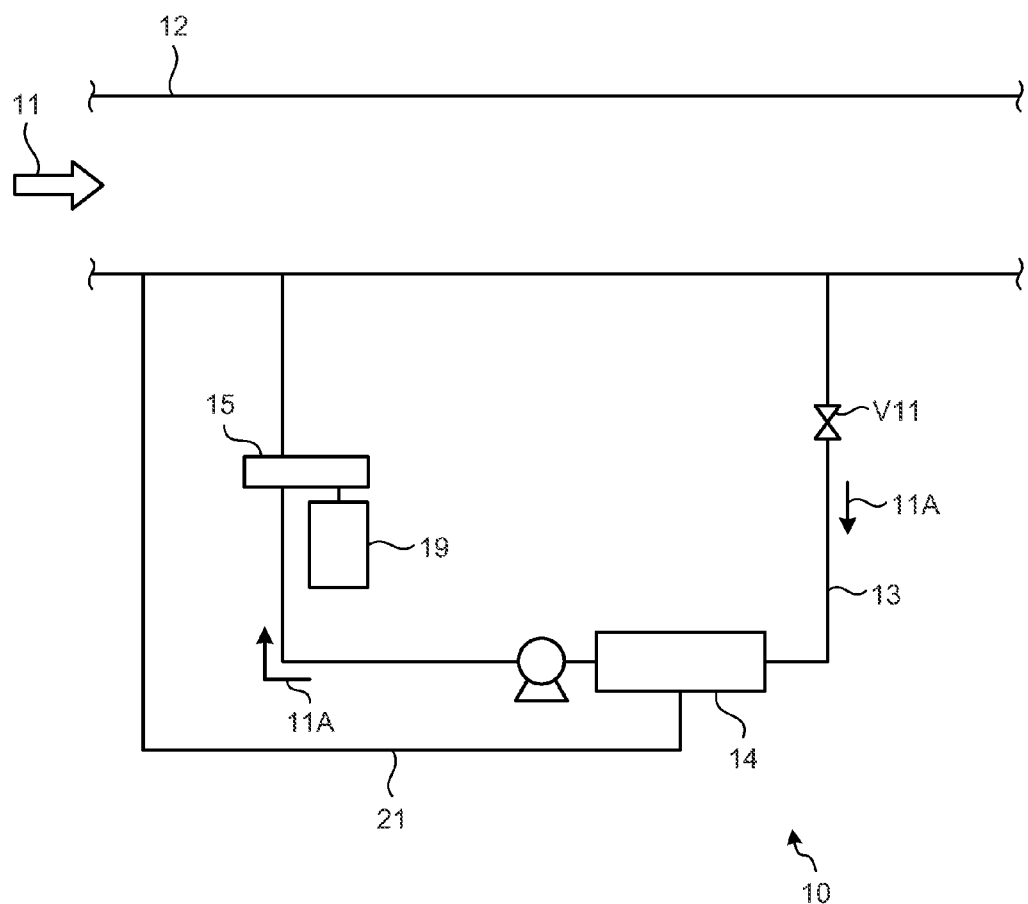
FIG. 1 is a schematic diagram of a gas analysis device according to a first embodiment of the present invention.
Figure 2:
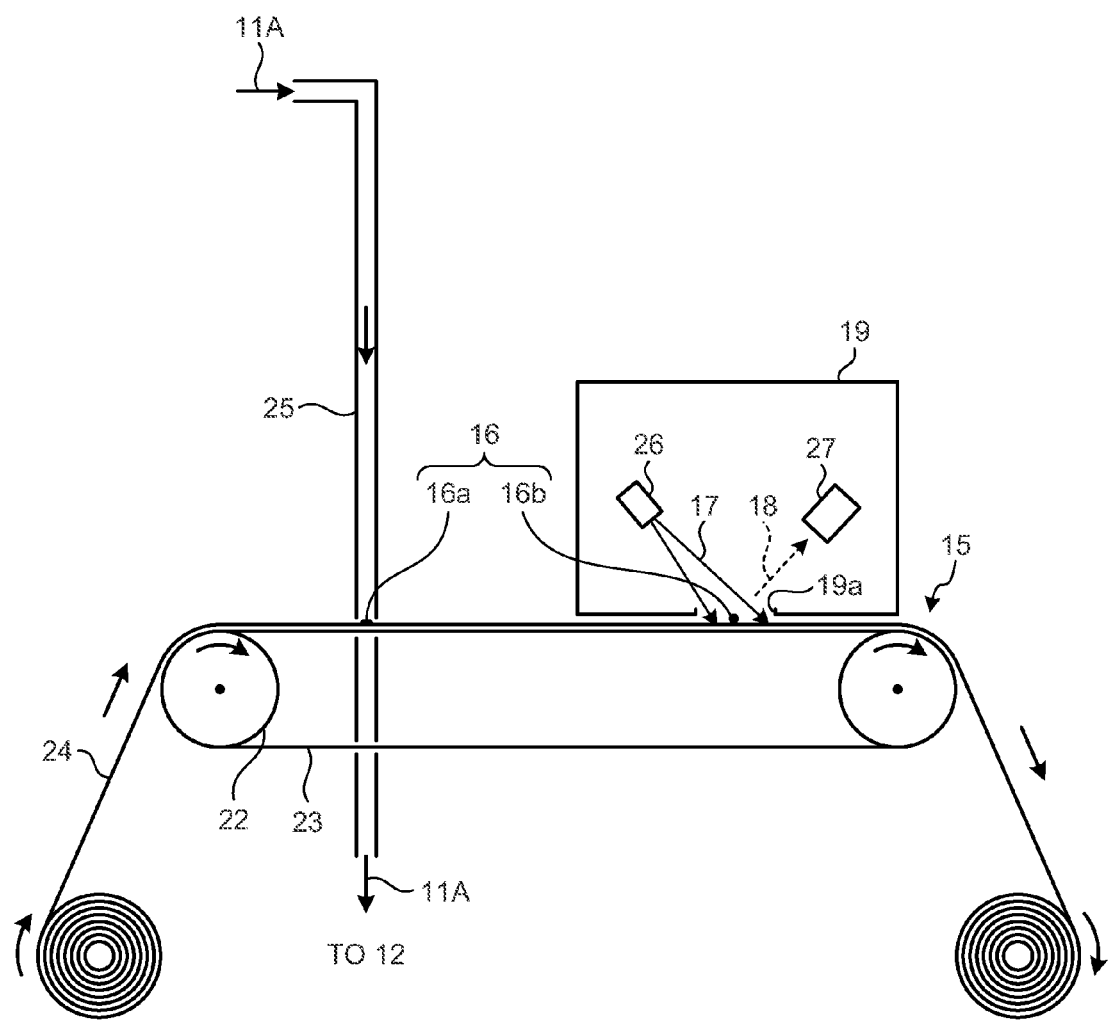
FIG. 2 depicts a configuration of a roll filter in a simplified manner.

A gas analysis device according to a first embodiment of the present invention is explained with reference to the drawings. FIG. 1 is a schematic diagram of a gas analysis device according to the first embodiment, and FIG. 2 depicts a configuration of a roll filter in a simplified manner. As shown in FIGS. 1 and 2, a gas analysis device 10 according to the present embodiment includes a flue-gas extraction pipe 13 that extracts flue gas 11A from a flue gas duct 12 to which flue gas 11 containing both of ammonium chloride ($NH_4Cl$) and sulfurous acid ($SO_3$) is fed, a collector (soot-dust removal means) 14 that is provided in the flue-gas extraction pipe 13 and removes soot dust contained in the extracted flue gas 11A, a roll filter (deposition means) 15 that is provided in the flue-gas extraction pipe 13 and deposits both of $NH_4Cl$ and $SO_3$ contained in the flue gas 11A, and a measurement device (measurement means) 19 that measures both of $NH_4Cl$ and $SO_3$ contained in the flue gas 11A by irradiating a sample 16 containing both of $NH_4Cl$ and $SO_3$ deposited by the roll filter 15 with X-rays 17 and detecting fluorescent X-rays 18 generated from the sample 16.

The flue gas 11 is emitted from a boiler and the flue gas 11 contains $SO_3$. Because an $NH_4Cl$ solution is supplied to the flue gas 11 within the flue gas duct 12, the flue gas 11 contains $NH_4Cl$. While gas components to be measured in the flue gas 11 contain both of $NH_4Cl$ and $SO_3$, the present embodiment is not limited thereto and it suffices that the flue gas 11 is gas containing at least $NH_4Cl$. The gas components contained in the flue gas 11 can contain also nitric oxide (NO), carbon monoxide (CO), water ($H_2O$), nitrogen dioxide ($NO_2$), methane ($CH_4$), ammonia, benzene, or the like, in addition to the $NH_4Cl$ and $SO_3$.

The flue-gas extraction pipe 13 is connected to the flue gas duct 12 and a part of the flue gas 11 flowing in the flue gas duct 12 is extracted through the flue-gas extraction pipe 13. An adjustment valve V11 is provided in the flue-gas extraction pipe 13 to adjust a flow rate of the flue gas 11 to be extracted from the flue gas duct 12 to the flue-gas extraction pipe 13. Because the flue gas 11 can be continuously extracted through the flue-gas extraction pipe 13, the gas components in the flue gas 11 can be semicontinuously measured.

The flue gas 11A extracted to the flue-gas extraction pipe 13 is fed to the collector 14 through the flue-gas extraction pipe 13. The collector 14 removes the soot dust contained in the flue gas 11A. While a cyclone dust-collection device is used, for example, as the collector 14, the present embodiment is not particularly limited thereto.

After the soot dust contained in the flue gas 11A is removed by the collector 14, the flue gas 11A is fed to the roll filter 15. The collector 14 has a soot-dust conveyance pipe 21 that emits the collected soot dust. The dust removed from the flue gas 11A by the collector 14 is returned from the soot-dust conveyance pipe 21 to the flue gas duct 12.

The roll filter 15 has a pair of rollers 22, a conveyance belt 23, a filter 24, and a flue-gas feed pipe 25. In the roll filter 15, the pair of rollers 22 rotates to rotate also the conveyance belt 23 and move the filter 24. The measurement device 19 analyzes concentrations of $NH_4Cl$ and $SO_3$ contained in the flue gas 11A. For example, a fluorescent X-ray analysis device is used as the measurement device 19. The measurement device 19 has an X-ray irradiation device 26 that irradiates the sample 16 with the X-rays 17, and a detector 27 that detects fluorescent X-rays 18 generated from the sample 16. The measurement device 19 has an opening 19a on the side of a wall surface on which the filter 24 is placed, and the filter 24 is irradiated with the X-rays 17 from the X-ray irradiation device 26 therethrough. The flue gas 11A fed from the flue-gas extraction pipe 13 to the flue-gas feed pipe 25 is fed to the filter 24. When the flue gas 11A passes through the filter 24, $NH_4Cl$ and $SO_3$ contained in the flue gas 11A is adsorbed by the filter 24 and a sample 16a containing both of $NH_4Cl$ and $SO_3$ is deposited on the filter 24. The sample 16a deposited on the roll filter 15 is conveyed to the measurement device 19 with movement of the filter 24. A sample 16b having moved near the opening 19a is irradiated with the X-rays 17 from the X-ray irradiation device 26 in the measurement device 19. $NH_4Cl$ and $SO_3$ contained in the sample 16b are excited with irradiation of the X-rays 17. The fluorescent X-rays 18 are generated from the excited $NH_4Cl$ and $SO_3$. The generated fluorescent X-rays 18 are detected and analyzed by the detector 27. The detector 27 analyzes $NH_4Cl$ and $SO_3$ contained in the flue gas 11A based on energy of the fluorescent X-rays 18 that are emitted when $NH_4Cl$ and $SO_3$ in the sample 16b is irradiated with the X-rays 17.

The measurement device 19 is not limited to the fluorescent X-ray analysis device and another analysis device can be used as long as it can analyze $NH_4Cl$ and $SO_3$ contained in the flue gas 11A.

Because the roll filter 15 deposits $NH_4Cl$ and $SO_3$ contained in the flue gas 11A in the flue-gas extraction pipe 13, it is preferable that the flue-gas feed pipe 25 through which the flue gas 11A flows have a heater on an outer circumference of the flue-gas feed pipe 25 and heat the flue gas 11A to prevent moisture contained in the flue gas 11A from condensing and analysis accuracy in the measurement device 19 from reducing.

The gas analysis device 10 according to the present embodiment deposits $NH_4Cl$ contained in the flue gas 11 and then analyzes the fluorescent X-rays 18 generated from the deposited $NH_4Cl$ and $SO_3$, thereby enabling the concentrations of ammonium ions ($NH_4^+$), chloride ions (Cl⁻), and $SO_3$ contained in the flue gas 11 to be stably and simultaneously analyzed. Accordingly, the concentrations of $NH_4Cl$ and $SO_3$ contained in the flue gas 11 can be stably and simultaneously measured. Therefore, when Hg contained in the flue gas 11 is to be oxidized, the concentration of the $NH_4Cl$ solution supplied into the flue gas duct 12 can be properly obtained even when the $NH_4Cl$ solution is supplied into the flue gas duct 12 in addition to $NH_3$ gas or $NH_3$ water.

While the solution including $NH_4Cl$ is used for the flue gas 11 in the gas analysis device 10 according to the present embodiment, the present embodiment is not limited thereto and any auxiliary agent can be used as long as it generates oxidizing gas to be used for oxidizing Hg when vaporized and reducing gas to be used for reducing NOx. Because the solution including $NH_4Cl$ is used in the present embodiment, the HCl gas is used as the oxidizing gas and the $NH_3$ gas is used as the reducing gas. Other than the solution including $NH_4Cl$, a solution including an ammonium halide such as ammonium bromide ($NH_4Br$) or ammonium iodide ($NH_4I$) can be used.

Second Embodiment

Figure 3:
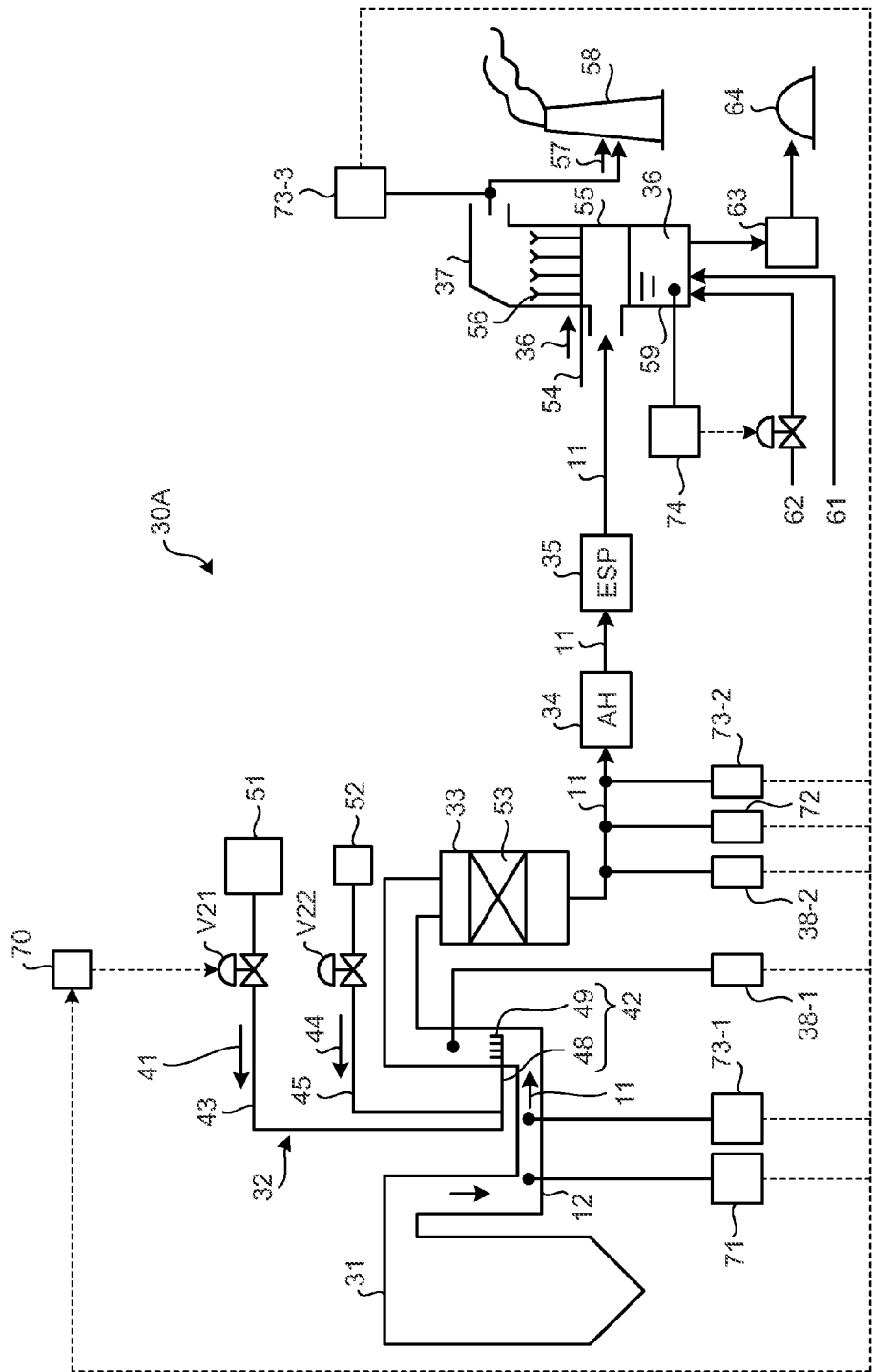
FIG. 3 is a schematic diagram of an Hg removal system according to a second embodiment of the present invention.

An Hg removal system according to a second embodiment of the present invention is explained with reference to the drawings. FIG. 3 is a schematic diagram of an Hg removal system according to the second embodiment. Because the Hg removal system according to the present embodiment uses the gas analysis device 10 according to the first embodiment shown in FIGS. 1 and 2 as an $NH_4Cl$ measurement device ($NH_4Cl$ measurement means), explanations of the $NH_4Cl$ measurement device will be omitted.

As shown in FIG. 3, an Hg removal system 30A according to the present embodiment is an Hg removal system that removes Hg contained in the flue gas 11 emitted from a boiler 31, and has an $NH_4Cl$-solution supply means 32 that sprays an $NH_4Cl$ solution 41, a reduction denitrator (reduction denitration means) 33 that has a denitration catalyst for reducing NOx in the flue gas 11 with $NH_3$ gas and oxidizing $Hg^0$ in coexistence of HCl gas, an air heater (AH) 34 that performs heat exchange with the denitrated flue gas 11, an electrostatic precipitator (ESP) 35 that removes soot dust in the denitrated flue gas 11, a wet desulfurizer 37 that removes Hg oxidized in the reduction denitrator 33 by using a limestone-gypsum slurry (alkali absorbent), and $NH_4Cl$ measurement devices ($NH_4Cl$ measurement means) 38-1 and 38-2 that are provided on upstream and downstream sides of the reduction denitrator 33 to analyze a concentration of $NH_4Cl$ contained in the flue gas 11, respectively, within the flue gas duct 12 downstream of the boiler 31.

The $NH_4Cl$ solution 41 is supplied from the $NH_4Cl$-solution supply means 32 to the flue gas 11 emitted from the boiler 31. The $NH_4CL$-solution supply means 32 has a spray nozzle 42 for oxidizing $Hg^0$ contained in the flue gas 11, an ammonium chloride ($NH_4Cl$)-solution supply pipe 43 that supplies the $NH_4Cl$ solution 41 in a liquid form to the spray nozzle 42, and an air supply pipe 45 that supplies air 44 to the spray nozzle 42 to compress the $NH_4Cl$ solution 41 to be sprayed into the flue gas duct 12.

Figure 4:
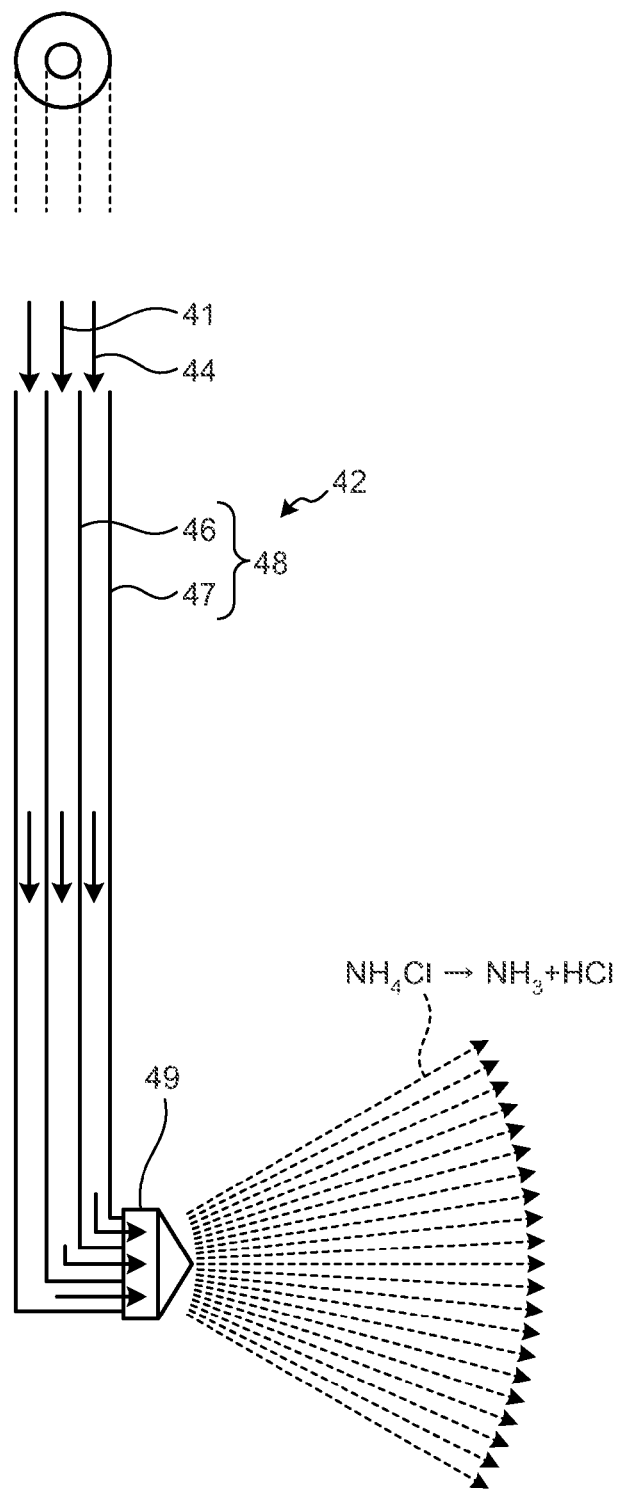
FIG. 4 schematically depicts a configuration of a spray nozzle.

The spray nozzle 42 is a two-fluid nozzle that is provided to be inserted into the flue gas duct 12 and simultaneously sprays the $NH_4Cl$ solution 41 and the air 44 into the flue gas duct 12. FIG. 4 schematically depicts a configuration of the spray nozzle. As shown in FIG. 4, the spray nozzle 42 is formed of a double pipe 48 including an inner pipe 46 and an outer pipe 47, and a nozzle head 49 provided at the head of the double pipe 48. The inner pipe 46 is used for feeding the $NH_4Cl$ solution 41. The outer pipe 47 is provided to cover an outer circumference of the inner pipe 46 and is used for feeding the air 44 into a space formed with the inner pipe 46. The spray nozzle 42 sprays the $NH_4Cl$ solution 41 into the flue gas duct 12 (see FIG. 3) and also sprays the air 44 into the flue gas duct 12, from the nozzle head 49.

As shown in FIG. 3, the $NH_4Cl$ solution 41 is fed from an $NH_4Cl$ solution tank 51 to the spray nozzle 42 through the $NH_4Cl$-solution supply pipe 43. A flow rate of the $NH_4Cl$ solution 41 supplied from the $NH_4Cl$-solution supply pipe 43 is adjusted by an adjustment valve V21. The $NH_4Cl$ solution 41 is adjusted in the $NH_4Cl$ solution tank 51 to have a predetermined concentration. The $NH_4Cl$ solution 41 can be generated by dissolving ammonia chloride ($NH_4Cl$) powder in water. The predetermined concentration of the $NH_4Cl$ solution 41 can be adjusted by adjusting supply amounts of the $NH_4Cl$ powder and the water. Alternatively, the $NH_4Cl$ solution 41 can be generated by mixing an HCl solution and an $NH_3$ solution in a predetermined proportion in concentration.

The air 44 is fed from an air supply unit 52 to the spray nozzle 42 through the air supply pipe 45 and is used as compression air when the $NH_4Cl$ solution 41 is sprayed from the nozzle head 49. By atomizing the $NH_4Cl$ solution 41 with an air stream of the air 44, the $NH_4Cl$ solution 41 to be sprayed from the nozzle head 49 can be sprayed as fine liquid droplets into the flue gas duct 12. A flow rate of the air 44 supplied from the air supply pipe 45 is adjusted by an adjustment valve V22.

As shown in FIG. 4, the liquid droplets of the $NH_4Cl$ solution 41 sprayed from the nozzle head 49 into the flue gas duct 12 evaporate due to a high ambient temperature of the flue gas 11 to generate fine solid particles of $NH_4Cl$, and decompose into HCl and $NH_3$ and sublimate as shown in the following formula (5). Accordingly, the $NH_4Cl$ solution 41 sprayed from the spray nozzle 42 is decomposed to generate HCl and $NH_3$, and $NH_3$ gas and HCl gas can be supplied into the flue gas duct 12.

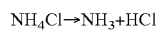

$$NH_4Cl \rightarrow NH_3 + HCl \qquad (5)$$

As shown in FIG. 3, the size of the liquid droplets of the $NH_4Cl$ solution 41 sprayed from nozzle holes of the nozzle head 49 can be adjusted by using the flow rate of the air 44 supplied from the air supply pipe 45. The flow rate of the air 44 sprayed from the nozzle head 49 is preferably an air/water ratio of 100 or higher and 10000 or lower (in volume), for example. This is to spray the $NH_4Cl$ solution 41 from the nozzle head 49 into the flue gas duct 12 as fine liquid droplets.

Because the air 44 flows in the space between the inner pipe 46 and the outer pipe 47 as shown in FIG. 4, the air 44 acts for cooling the $NH_4Cl$ solution 41 and can suppress heat of the flue gas 11 in the flue gas duct 12 from being transmitted to the $NH_4Cl$ solution 41 via the air 44 as shown in FIG. 3. Because heating of the $NH_4Cl$ solution 41 by the heat of the flue gas 11 can be suppressed, the $NH_4Cl$ solution 41 can be kept in a liquid state until immediately before it is sprayed.

As shown in FIG. 3, after being caused to contain the HCl gas and the $NH_3$ gas that is generated from the liquid droplets of the $NH_4Cl$ solution 41 sprayed from the $NH_4Cl$-solution supply means 32 into the flue gas duct 12, the flue gas 11 is fed to the reduction denitrator 33. The reduction denitrator 33 uses the $NH_3$ gas generated by decomposition of $NH_4Cl$ for reduction denitration of NOx and uses the HCl gas for oxidation of Hg, thereby removing NOx and Hg from the flue gas 11.

That is, on the denitration catalyst filled in the reduction denitrator 33, the $NH_3$ gas reductively denitrates NOx as shown in the following formula (6) and the HCl gas performs mercury oxidation of Hg as shown in the following formula (7).

$$4NO+4NH_3+O_2 \rightarrow 4N_2+6H_2O \quad (6)$$

$$Hg+\tfrac{1}{2}O_2+2HCl \rightarrow HgCl_2+H_2O \quad (7)$$

While the reduction denitrator 33 has one denitration catalyst layer 53, the present embodiment is not limited thereto and the number of denitration catalyst layers 53 in the reduction denitrator 33 can be appropriately changed according to denitration performance.

After reduction of NOx and oxidation of Hg in the flue gas 11 is performed in the reduction denitrator 33, the flue gas 11 passes through the air heater 34 and the precipitator (ESP) 35 and then is fed to the wet desulfurizer 37.

In the wet desulfurizer 37, the flue gas 11 is fed from the wall surface side of a bottom portion in a device body 55, and a limestone-gypsum slurry 36 to be used as the alkali absorbent is fed into the device body 55 through an absorbent feed line 54 to be jetted from a nozzle 56 toward a top portion. The flue gas 11 rising from the bottom portion of the device body 55 and the limestone-gypsum slurry 36 jetted from the nozzle 56 to flow down is caused to face each other to be in gas-liquid contact, and $HgCl_2$ and sulfur oxides (SOx) in the flue gas 11 are absorbed in the limestone-gypsum slurry 36 to be separated and removed from the flue gas 11, thereby cleaning the flue gas 11. The flue gas 11 cleaned by the limestone-gypsum slurry 36 is emitted from the top portion as cleaned gas 57 and discharged from a stack 58 to outside of the system.

The limestone-gypsum slurry 36 used to desulfurize the flue gas 11 is generated by mixing limestone slurry $CaCO_3$, which is obtained by dissolving limestone powder in water, gypsum slurry $CaSO_4$, which is obtained by causing limestone and SOx in the flue gas 11 to react with each other and to be oxidized, and water. The limestone-gypsum slurry 36 is used by pumping the fluid stored in a bottom portion 59 of the device body 55 of the wet desulfurizer 37, for example. SOx in the flue gas 11 reacts with the limestone-gypsum slurry 36 in the device body 55 as shown in the following formula (8).

$$CaCO_3+SO_2+0.5H_2O \rightarrow CaSO_3 \cdot 0.5H_2O+CO_2 \quad (8)$$

Meanwhile, the limestone-gypsum slurry 36 that has absorbed SOx in the flue gas 11 is mixed with water 61 supplied into the device body 55 and is oxidized by air 62 supplied into the bottom portion 59 of the device body 55.

At that time, the limestone-gypsum slurry 36 having flowed down in the device body 55 reacts with the water 61 and the air 62 as shown in the following formula (9).

$$CaSO_3 \cdot 0.5H_2O+0.5O_2+1.5H_2O \rightarrow CaSO_4 \cdot 2H_2O \quad (9)$$

The limestone-gypsum slurry 36 being stored in the bottom portion 59 of the wet desulfurizer 37 and having been used for desulfurization is oxidized, then drawn off from the bottom portion 59, fed to a dewaterer 63, and then discharged to outside of the system as dewatered cake (gypsum) 64 including mercury chloride (HgCl). For example, a belt filter is used as the dewaterer 63. Filtrate obtained by dewatering (post-dewatering filtrate) is subjected to effluent treatment such as removal of suspended solids and heavy metals in the post-dewatering filtrate and pH adjustment of the post-dewatering filtrate. A part of the post-dewatering filtrate subjected to the effluent treatment is returned to the wet desulfurizer 37 and the remaining part of the post-dewatering filtrate is treated as water discharge.

While the limestone-gypsum slurry 36 is used as the alkali absorbent, any solution can be used as the alkali absorbent as long as it can absorb $HgCl_2$ in the flue gas 11.

The limestone-gypsum slurry 36 does not always need to be jetted toward the top portion from the nozzle 56 and can be flowed down from the nozzle 56 to face the flue gas 11, for example.

(Control of Spray Amount of $NH_4Cl$ Solution)

The $NH_4Cl$ measurement device 38-1 is provided on the upstream side of the reduction denitrator 33, and the $NH_4Cl$ measurement device 38-2 is provided on the downstream side of the reduction denitrator 33. The $NH_4Cl$ measurement devices 38-1 and 38-2 use the gas analysis device 10 according to the first embodiment shown in FIGS. 1 and 2, as mentioned above. Therefore, the $NH_4Cl$ measurement devices 38-1 and 38-2 can analyze the concentration of $NH_4Cl$ supplied from the spray nozzle 42 into the flue gas 11. For example, when the boiler 31 is a coal combustion boiler 31, the flue gas 11 contains also $SO_3$. The $NH_4Cl$ measurement devices 38-1 and 38-2 can measure also the concentration of $SO_3$ contained in the flue gas 11 and accordingly the $NH_4Cl$ measurement devices 38-1 and 38-2 can simultaneously measure the concentrations of $NH_4Cl$ and $SO_3$ contained in the flue gas 11.

Measurement results of the concentration of $NH_4Cl$ contained in the flue gas 11, measured by the $NH_4Cl$ measurement devices 38-1 and 38-2, are transmitted to a controller 70. A map indicating a relation between $NH_4Cl$ concentrations and gas temperatures at which $NH_4Cl$ deposits and a map indicating a relation between $SO_3$ concentrations and gas temperatures at which $SO_3$ deposits, which are obtained in advance, are recorded in the controller 70. For example, the gas temperature at which $NH_4Cl$ deposits increases as the $NH_4Cl$ concentration increases, and the gas temperature at which $SO_3$ deposits increases as the $SO_3$ concentration increases. When the map indicating the relation between $NH_4Cl$ concentrations and gas temperatures at which $NH_4Cl$ deposits and the map indicating the relation between $SO_3$ concentrations and gas temperatures at which $SO_3$ deposits are obtained in advance, the gas temperature can be adjusted according to the $NH_4Cl$ concentration or the $SO_3$ concentration to prevent deposition of $NH_4Cl$ or $SO_3$.

The controller 70 can obtain the concentration of $NH_4Cl$ contained in the flue gas 11 by analyzing the concentration of $Cl^-$ contained in the flue gas 11 based on the map indicating the relation between $NH_4Cl$ concentrations and gas temperatures at which $NH_4Cl$ deposits, which is obtained in advance from the measurement results of the concentration of $NH_4Cl$ contained in the flue gas 11, measured by the $NH_4Cl$ measurement devices 38-1 and 38-2. By obtaining the concentration of $NH_4Cl$ contained in the flue gas 11, the controller 70 can control the spray amount of the $NH_4Cl$ solution, so that the $NH_4Cl$ solution can be sprayed from the spray nozzle 42 in an appropriate spray amount.

Because the $NH_4Cl$ measurement devices 38-1 and 38-2 can measure also the concentration of $SO_3$ in addition to the concentration of $NH_4Cl$ contained in the flue gas 11, the $NH_4Cl$ measurement devices 38-1 and 38-2 transmit the concentration of $SO_3$ contained in the flue gas 11 to the controller 70. The controller 70 can obtain the concentration of $SO_3$ contained in the flue gas 11 by analyzing the concentration of $SO_3$ contained in the flue gas 11 based on the map indicating the relation between $SO_3$ concentrations and gas temperatures at which $SO_3$ deposits, which is obtained in advance from measurement results of the concentration of $SO_3$ contained in the flue gas 11, measured by the $NH_4Cl$ measurement devices 38-1 and 38-2. By obtaining the concentration of $SO_3$ contained in the flue gas 11, the controller 70 can control the spray amount of the NH$_4$Cl solution, so that the NH$_4$Cl solution can be sprayed from the spray nozzle 42 in an appropriate spray amount.

As described above, the Hg removal system 30A to which a spray device is applied according to the present embodiment can stably and simultaneously analyze the concentrations of NH$_4^+$, CL$^-$, and SO$_3$ contained in the flue gas 11 and thus can stably and simultaneously measure the concentrations of NH$_4$Cl and SO$_3$ contained in the flue gas 11. Therefore, the NH$_4$Cl solution 41 can be sprayed from the spray nozzle 42 into the flue gas duct 12 in an appropriate amount and accordingly Hg removal performance and NOx reduction performance can be stably maintained in the reduction denitrator 33. Corrosion of spray facilities such as the outer pipe 47 of the spray nozzle 42 can be avoided, which realizes a stable operation and also enables lives of devices such as the spray nozzle 42 to be extended and costs required for maintenance of the devices to be reduced. Furthermore, when an NH$_3$-water supply means that supplies NH$_3$ water into the flue gas duct 12 is installed, the concentration of the NH$_4$Cl solution supplied into the flue gas duct 12 can be appropriately obtained even when the NH$_4$Cl-solution supply means 32 is newly installed in the flue gas duct 12.

A flowmeter 71 that measures a flow rate of the flue gas 11 is provided on the upstream side of the spray nozzle 42. The flow rate of the flue gas 11 is measured by the flowmeter 71. The value of the flow rate of the flue gas 11 measured by the flowmeter 71 is transmitted to the controller 70 and the flow rate, angle, initial velocity, and the like, at which the NH$_4$Cl solution 41 is to be sprayed from the nozzle head 49 can be adjusted based on the flow rate value of the flue gas 11.

An NOx concentration meter 72 is provided on the side of an outlet of the reduction denitrator 33. The value of the concentration of NOx in the flue gas 11 measured by the NOx concentration meter 72 is transmitted to the controller 70. The controller 70 can check a NOx reduction ratio in the reduction denitrator 33 based on the concentration value of NOx in the flue gas 11 measured by the NOx concentration meter 72. Therefore, based on the value of the concentration of NOx in the flue gas 11 measured by the NOx concentration meter 72, the NH$_4$Cl concentration and the supply amount of the NH$_4$Cl solution 41 sprayed from the spray nozzle 42 can be adjusted and also the supply amount of the NH$_3$ water separately supplied into the flue gas 11 can be adjusted to adjust an NH$_3$ mixture ratio. Accordingly, NOx in the flue gas 11 can be reduced in the reduction denitrator 33 and the reduction denitrator 33 can meet predetermined denitration performance.

Hg concentration meters 73-1 to 73-3 that measure content of Hg in the flue gas 11 emitted from the boiler 31 are provided in the flue gas duct 12. The Hg concentration meter 73-1 is provided in the flue gas duct 12 between the boiler 31 and the nozzle head 49, the Hg concentration meter 73-2 is provided between the reduction denitrator 33 and the air heater 34, and the Hg concentration meter 73-3 is provided on the downstream side of the wet desulfurizer 37. Values of the concentration of Hg in the flue gas 11 measured by the Hg concentration meters 73-1 to 73-3 are transmitted to the controller 70. The controller 70 can check the content of Hg contained in the flue gas 11 from the values of the concentration of Hg in the flue gas 11 measured by the Hg concentration meters 73-1 to 73-3. Specifically, the Hg concentration meters 73-1 to 73-3 each can optionally measure metallic mercury Hg$^0$, mercury oxide Hg$^{2+}$, and total mercury (an amount of mercury including the metallic mercury Hg$^0$ and the mercury oxide Hg$^{2+}$). When a ratio of the mercury oxide Hg$^{2+}$ to the total mercury is known by using the Hg concentration meters 73-2 and 73-3, a mercury oxidation rate of Hg contained in the flue gas 11 can be obtained. By controlling the NH$_4$Cl concentration and the supply flow rate of the NH$_4$Cl solution 41 based on the values of the concentration of Hg in the flue gas 11 measured by the Hg concentration meters 73-1 to 73-3 and the mercury oxidation rate, the NH$_4$Cl concentration and the supply flow rate of the NH$_4$Cl solution 41 sprayed from the nozzle head 49 can be controlled to meet predetermined denitration performance and keep Hg oxidation performance.

An oxidation-reduction-potential measurement controller (ORP controller) 74 that measures an oxidation-reduction potential of the limestone-gypsum slurry 36 is provided in the bottom portion 59 of the wet desulfurizer 37. The value of the oxidation-reduction potential of the limestone-gypsum slurry 36 is measured by the ORP controller 74. The supply amount of the air 62 to be supplied into the bottom portion 59 of the wet desulfurizer 37 is adjusted based on the measured value of the oxidation-reduction potential. By adjusting the supply amount of the air 62 to be supplied into the bottom portion 59, reduction of oxidized Hg collected in the limestone-gypsum slurry 36 that is stored in the bottom portion 59 of the wet desulfurizer 37 and diffusion thereof from the stack 58 can be prevented.

The oxidation-reduction potential of the limestone-gypsum slurry 36 in the wet desulfurizer 37 is preferably in a range of no less than 0 millivolt and no larger than 600 millivolts, for example, to prevent re-entrainment of Hg from the limestone-gypsum slurry 36. When the oxidation-reduction potential is in this range, Hg collected as HgCl$_2$ in the limestone-gypsum slurry 36 is stabilized and re-entrainment into air can be prevented.

While the solution including NH$_4$Cl is used to oxidize Hg and reduce NOx in the Hg removal system 30A according to the present embodiment, the present embodiment is not limited thereto and a solution including ammonium halide such as NH$_4$Br or NH$_{4I}$ can be used other than the solution including NH$_4$Cl, as mentioned above.

Third Embodiment

Figure 5:
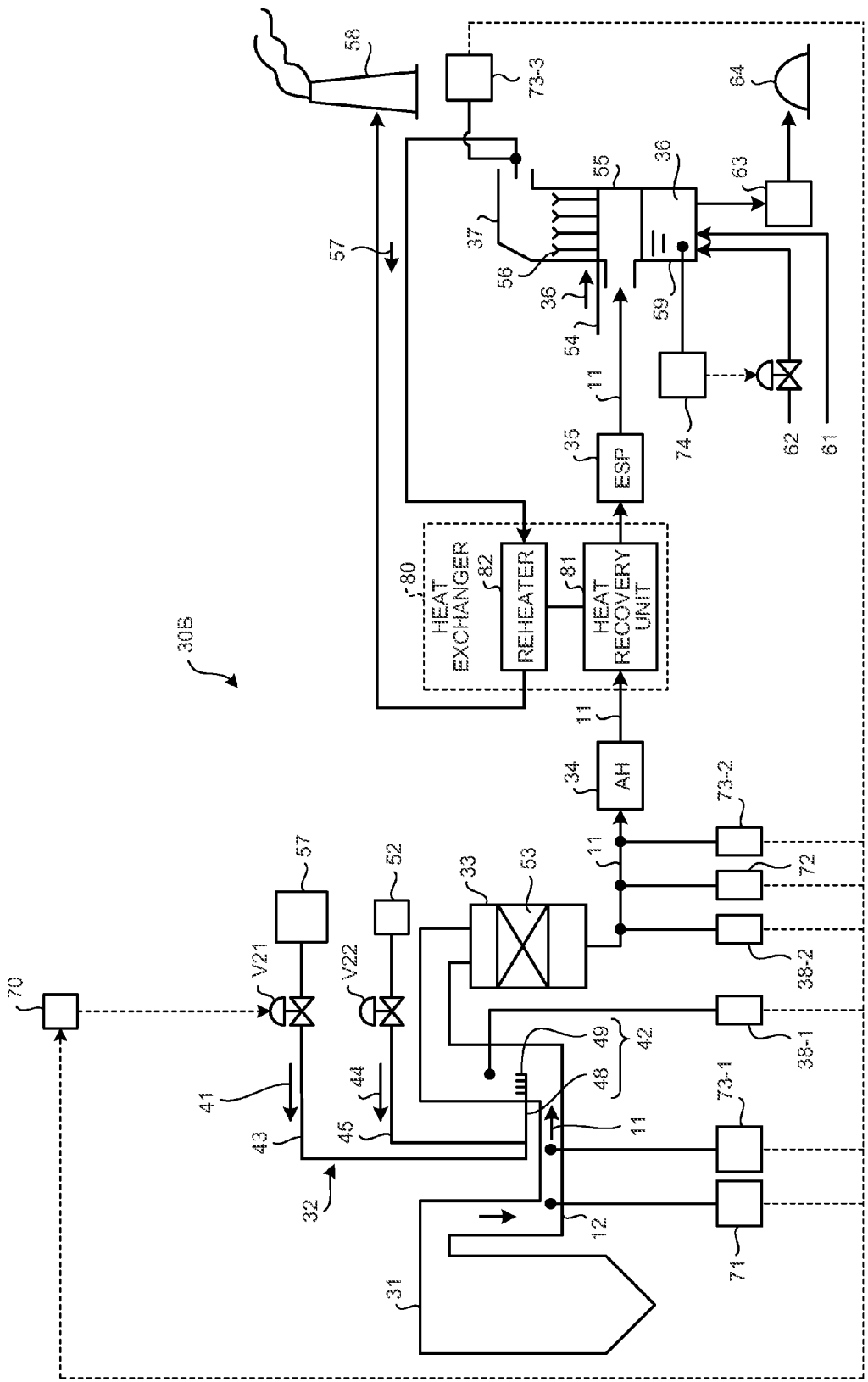
FIG. 5 depicts a configuration of an Hg removal system according to a third embodiment of the present invention.
Figure 6:
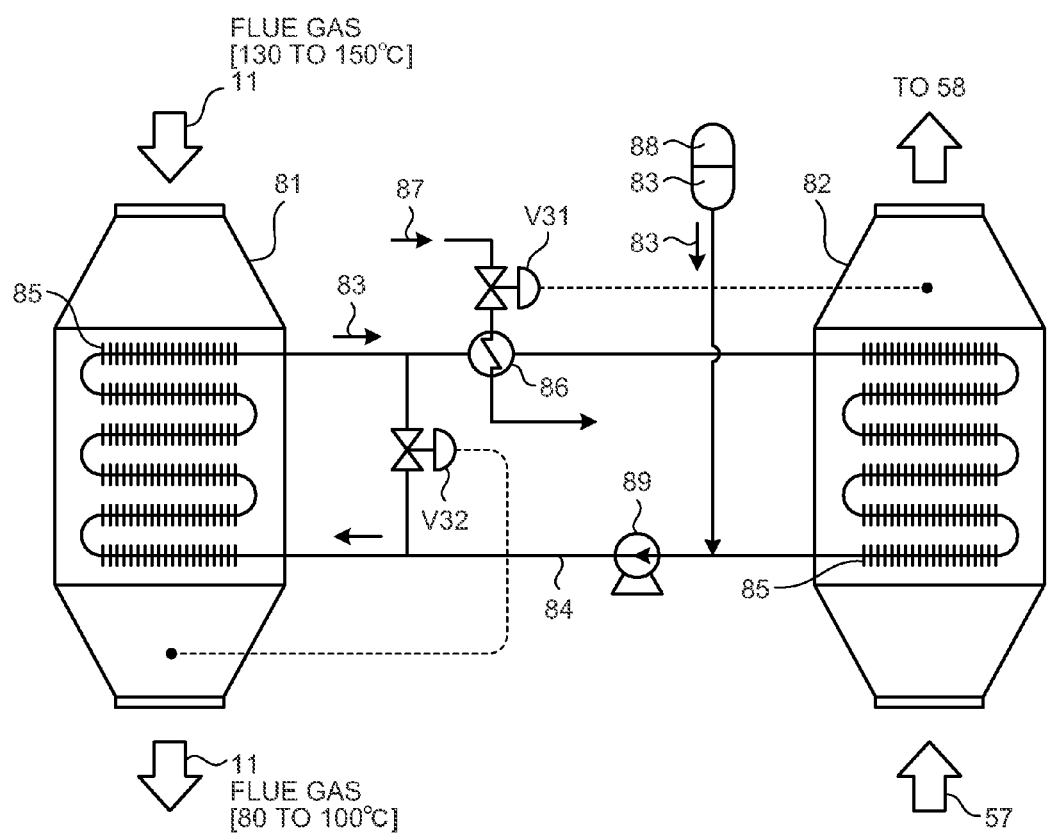
FIG. 6 depicts a configuration of a heat exchanger in a simplified manner.

An Hg removal system to which a spray device is applied according to a third embodiment of the present invention is explained with reference to the drawings. FIG. 5 depicts a configuration of the Hg removal system according to the third embodiment, and FIG. 6 depicts a configuration of a heat exchanger in a simplified manner. Members of the Hg removal system that are redundant to constituent elements in the Hg removal system according to the second embodiment of the present invention are denoted by like reference signs and explanations thereof will be omitted.

As shown in FIGS. 5 and 6, an Hg removal system 30B according to the present embodiment has a heat exchanger 80 installed between the air heater 34 and the precipitator 35 to perform heat exchange with the flue gas 11 having passed through the reduction denitrator 33 for heat recovery. The heat exchanger 80 includes a heat recovery unit 81 and a reheater 82. The heat recovery unit 81 is provided between the air heater 34 and the precipitator 35 and performs heat exchange between the flue gas 11 emitted from the boiler 31 and a heating medium 83 circulating in the heat exchanger 80. The gas temperature of the flue gas 11 emitted from the boiler 31 is in a range between 130° C. to 150° C., for example, and the gas temperature of the flue gas 11 emitted from the heat recovery unit 81 falls in a range between 80° C. to 100° C., for example, by the heat exchange of the flue gas 11 with the heating medium 83 circulating in the heat exchanger 80. The reheater 82 is provided on the downstream side of the wet desulfurizer 37 and performs heat exchange between the cleaned gas 57 emitted from the wet desulfurizer 37 and the heating medium 83 to reheat the cleaned gas 57.

The heat exchanger 80 has a heating-medium circulating passage 84 for the heating medium 83 to circulate through the heat recovery unit 81 and the reheater 82. The heating medium 83 circulates between the heat recovery unit 81 and the reheater 82 via the heating-medium circulating passage 84. A plurality of finned tubes 85 are provided on the surface of the heating-medium circulating passage 84 located within the heat recovery unit 81 and the reheater 82. A heat exchange unit 86 is provided on the heating-medium circulating passage 84 and heat exchange of the heating medium 83 with steam 87 is performed to adjust a medium temperature of the heating medium 83.

Because the concentration of $NH_4Cl$ and the concentration of $SO_3$ contained in the flue gas 11 can be measured by the $NH_4Cl$ measurement devices 38-1 and 38-2, the controller 70 increases the medium temperature of the heating medium 83 by causing the heat exchange unit 86 to perform heat exchange of the heating medium 83 with the steam 87 based on either one or both of the map indicating the relation between $NH_4Cl$ concentrations and gas temperatures at which $NH_4Cl$ deposits or the map indicating the relation between $SO_3$ concentrations and gas temperatures at which $SO_3$ deposits, which are obtained in advance. When the gas temperature of the flue gas 11 on the outlet side of the heat recovery unit 81 is set to be equal to or higher than the gas temperature at which the $NH_4Cl$ and $SO_3$ deposit, deposition of $SO_3$ on the finned tubes 85 of the heat recovery unit 81 can be suppressed. Accordingly, corrosion of the finned tubes 85 of the heat recovery unit 81 can be suppressed.

When the amount of the heating medium 83 flowing in the heat recovery unit 81 is reduced, a heat recovery amount recovered by the heating medium 83 in the heat recovery unit 81 is reduced and thus the heat recovery unit 81 keeps a high outlet gas temperature. Because an amount of heat of the heating medium 83 flowing in the reheater 82 is small in this case, the temperature of the cleaned gas 57 entering the reheater 82 cannot be increased. Accordingly, to increase the temperature of the cleaned gas 57 having passed through the reheater 82, an amount of the steam 87 to be added is increased to increase the heat amount of the heating medium 83 flowing in the reheater 82, so that the temperature of the cleaned gas 57 passing through the reheater 82 can be increased.

When the amount of the heating medium 83 flowing in the heat recovery unit 81 is increased, the heat recovery amount recovered by the heating medium 83 in the heat recovery unit 81 is increased. Accordingly, the outlet gas temperature of the flue gas 11 exiting the heat recovery unit 81 is lowered and the temperature of the heating medium 83 flowing in the reheater 82 is increased, which increases the temperature of the cleaned gas 57 entering the reheater 82. Therefore, the supply amount of the steam 87 supplied for heat exchange with the heating medium 83 can be reduced.

The heating medium 83 is supplied to the heating-medium circulating passage 84 from a heating medium tank 88. The heating medium 83 is circulated through the heating-medium circulating passage 84 by a heating-medium feed pump 89. The supply amount of the steam 87 is adjusted by an adjustment valve V31 according to the gas temperature of the cleaned gas 57, and the heating medium 83 to be fed to the reheater 82 is supplied to the heat recovery unit 81 by an adjustment valve V32 according to the gas temperature of the flue gas 11 emitted from the heat recovery unit 81, thereby adjusting the supply amount of the heating medium 83 to be fed to the reheater 82.

Therefore, the concentration of $NH_4Cl$ and the concentration of $SO_3$ contained in the flue gas 11 are measured by the $NH_4Cl$ measurement devices 38-1 and 38-2, the medium temperature of the heating medium 83 is increased based on either one or both of the map indicating the relation between $NH_4Cl$ concentrations and gas temperatures at which $NH_4Cl$ deposits and the map indicating the relation between $SO_3$ concentrations and gas temperatures at which $SO_3$ deposits, which are obtained in advance, and the gas temperature of the flue gas 11 on the outlet side of the heat recovery unit 81 is set to be equal to or higher than the gas temperature at which $NH_4Cl$ and $SO_3$ deposits. Accordingly, deposition of $NH_4Cl$ and $SO_3$ on facilities installed within the flue gas duct 12, such as the finned tubes 85 of the heat recovery unit 81, can be suppressed and corrosion of the finned tubes 85 of the heat recovery unit 81 and the like can be suppressed.

While the heat exchanger 80 is provided between the air heater 34 and the precipitator 35 in the present embodiment, the present embodiment is not limited thereto and it suffices to provide the heat exchanger 80 between the reduction denitrator 33 and the wet desulfurizer 37.

REFERENCE SIGNS LIST 10 gas analysis device
11, 11A flue gas
12 flue gas duct
13 flue-gas extraction pipe
14 collector (soot-dust removal means)
15 roll filter (deposition means)
16, 16a, 16b sample
17 X-ray
18 fluorescent X-ray
19 measurement device (measurement means)
19a opening
21 soot-dust conveyance pipe
22 roller
23 conveyance belt
24 filter
25 flue-gas feed pipe
26 X-ray irradiation device
27 detector
30A, 30B Hg removal system
31 boiler
32 $NH_4Cl$-solution supply means
33 reduction denitrator (reduction denitration means)
34 air heater (AH)
35 electrostatic precipitator (ESP)
36 limestone-gypsum slurry (alkali absorbent)
37 wet desulfurizer
38-1, 38-2 $NH_4Cl$ measurement device ($NH_4Cl$ measurement means)
41 $NH_4Cl$ solution
42 spray nozzle
43 ammonium chloride ($NH_4Cl$)-solution supply pipe
44 air
45 air supply pipe
46 inner pipe
47 outer pipe
48 double pipe
49 nozzle head
51 ammonium chloride ($NH_4Cl$) solution tank
52 air supply unit
53 denitration catalyst layer 54 absorbent feed line
55 device body
56 nozzle
57 cleaned gas
58 stack
59 bottom portion
61 water
62 air
63 dewaterer
64 dewatered cake (gypsum)
70 controller
71 flowmeter
72 NOx concentration meter
73-1 to 73-3 mercury (Hg) concentration meter
74 oxidation-reduction-potential measurement controller (ORP controller)
80 heat exchanger
81 heat recovery unit
82 repeater
83 heating medium
84 heating-medium circulating passage
85 finned tube
86 heat exchange unit
87 steam
88 heating medium tank
V11, V21, V22, V31, V32 adjustment valve

The invention claimed is:

1. A gas analysis device comprising:
a flue-gas extraction pipe for extracting, from a flue gas duct, flue gas that is emitted from a boiler and to which ammonium chloride is supplied;
soot-dust removal unit that is provided in the flue-gas extraction pipe, for removing soot dust contained in the extracted flue gas;
a deposition unit that is provided in the flue-gas extraction pipe, for depositing the ammonium chloride contained in the flue gas; and
a measurement unit for measuring the ammonium chloride contained the flue gas by detecting fluorescent X-rays generated by irradiation of the ammonium chloride deposited by the deposition unit with X-rays or laser beams.

2. The gas analysis device according to claim 1, wherein the flue gas further contains sulfurous acid, the deposition unit deposits sulfurous acid, and the measurement unit measures sulfurous acid.

3. A mercury removal system for removing mercury contained in flue gas that is emitted from a boiler, the mercury removal system comprising:
an ammonium-chloride supply unit for spraying a solution containing ammonium chloride into a flue gas duct of the boiler;
a reduction denitrator including a denitration catalyst for reducing nitrogen oxides in the flue gas with ammonia and for oxidizing mercury in coexistence of hydrogen chloride;
a wet desulfurizer for removing the mercury oxidized in the reduction denitrator using an alkali absorbent; and
an ammonium-chloride-concentration measurement unit that is provided on either one or both of upstream and downstream sides of the reduction denitrator, for analyzing a concentration of the ammonium chloride contained in the flue gas, wherein
the gas analysis device according to claim 1 is used as the ammonium-chloride-concentration measurement unit, and
a spray amount of the solution containing the ammonium chloride is controlled according to the concentration of the ammonium chloride obtained by the ammonium-chloride-concentration measurement unit.

4. The mercury removal system according to claim 3 further comprising a heat exchanger that is provided between the reduction denitrator and the wet desulfurizer, for performing heat exchange with the flue gas having passed through the reduction denitrator for heat recovery, wherein
a gas temperature of the flue gas through the heat exchanger is controlled based on a relation between ammonium chloride concentrations and gas temperatures, which are obtained in advance.

5. The mercury removal system according to claim 3, having further comprising a heat exchanger that is provided between the reduction denitrator and the wet desulfurizer, for performing heat exchange with the flue gas having passed through the reduction denitrator for heat recovery, wherein
the flue gas further contains sulfurous acid, the deposition unit deposits sulfurous acid, and the measurement unit measures sulfurous acid, and
a gas temperature of the flue gas passing through the heat exchanger is controlled based on either one or both of a relation between ammonium chloride concentrations and gas temperatures and a relation between sulfurous acid concentrations and gas temperatures, which are obtained in advance.

6. A mercury removal method for removing mercury contained in flue gas emitted from a boiler,
the mercury removal method comprising:
spraying a solution containing ammonium chloride into a flue gas duct of the boiler;
reducing nitrogen oxides in the flue gas with ammonia and oxidizing mercury in coexistence of hydrogen chloride;
removing the oxidized mercury using an alkali absorbent; and
analyzing a concentration of the ammonium chloride contained in the flue gas on either one or both of upstream and downstream sides of the reduction denitrator,
wherein at the analyzing the concentration of the ammonium chloride, a gas analysis method is used, the gas analysis method comprising:
extracting, from a flue gas duct, flue gas that is emitted from a boiler and to which ammonium chloride is supplied;
removing soot dust contained in the flue gas;
depositing the ammonium chloride contained in the flue gas;
causing the deposited ammonium chloride to be contained in analysis gas;
extracting the analysis gas; and
measuring the ammonium chloride contained in the analysis gas,
wherein a concentration of the ammonium chloride contained in the flue gas is obtained at the analyzing the concentration of the ammonium chloride, and a spray amount of the solution containing the ammonium chloride is controlled according to the obtained concentration of the ammonium chloride, and
wherein the mercury removal method further comprising:
heat-exchanging between the flue gas and a heating medium circulating in a heat exchanger between the reducing nitrogen oxides and the removing the oxidized mercury; and
reheating cleaned gas emitted from the wet desulfurizer by heat-exchanging between the cleaned gas and the heating medium, wherein a gas temperature of the flue gas to be subjected to heat exchange with the heating medium at the heat-exchanging is controlled based on a relation between ammonium chloride concentrations and gas temperatures, which are obtained in advance.

7. A mercury removal method for removing mercury contained in flue gas emitted from a boiler, the mercury removal method comprising:

spraying a solution containing ammonium chloride into a flue gas duct of the boiler;

reducing nitrogen oxides in the flue gas with ammonia and oxidizing mercury in coexistence of hydrogen chloride;

removing the oxidized mercury using an alkali absorbent; and analyzing a concentration of the ammonium chloride contained in the flue gas on either one or both of upstream and downstream sides of the reduction denitrator, wherein at the analyzing the concentration of the ammonium chloride, a gas analysis method is used, the gas analysis method comprising:

extracting, from a flue gas duct, flue gas that is emitted from a boiler and to which ammonium chloride is supplied;

removing soot dust contained in the flue gas;

depositing the ammonium chloride contained in the flue gas;

causing the deposited ammonium chloride to be contained in analysis gas;

extracting the analysis gas; and measuring the ammonium chloride contained in the analysis gas, wherein a concentration of the ammonium chloride contained in the flue gas is obtained at the analyzing the concentration of the ammonium chloride, and a spray amount of the solution containing the ammonium chloride is controlled according to the obtained concentration of the ammonium chloride, and wherein the mercury removal method further comprising:

heat-exchanging between the flue gas and a heating medium circulating in a heat exchanger between the reducing nitrogen oxides and the removing the oxidized mercury; and reheating cleaned gas emitted from the wet desulfurizer by heat-exchanging between the cleaned gas and the heating medium, wherein the gas analysis method, wherein the flue gas further contains sulfurous acid, the sulfurous acid is deposited in addition to the ammonium chloride, and the deposited sulfurous acid is measured, is used at the analyzing the concentration of the ammonium chloride, and a gas temperature of the flue gas subjected to heat exchange with the heating medium at the heat-exchanging is controlled based on either one or both of a relation between ammonium chloride concentrations and gas temperatures and a relation between sulfurous acid concentrations and gas temperatures, which are obtained in advance.

* * * * *